(12) United States Patent
Avey et al.

(10) Patent No.: US 9,707,416 B2
(45) Date of Patent: Jul. 18, 2017

(54) ANTIPERSPIRANT PRODUCTS

(75) Inventors: Ryan Joseph Avey, Cincinnati, OH (US); Michael John Bolander, Loveland, OH (US); Joseph Estill Lennon, Glendale, OH (US); David William Walling, Cincinnati, OH (US); Steven Michael Wujek, Bel Aire, MD (US)

(73) Assignee: The Procter & Gamble Company, Cincinnati, OH (US)

( * ) Notice: Subject to any disclaimer, the term of this patent is extended or adjusted under 35 U.S.C. 154(b) by 1477 days.

(21) Appl. No.: 12/364,213

(22) Filed: Feb. 2, 2009

(65) Prior Publication Data
US 2010/0196299 A1    Aug. 5, 2010

(51) Int. Cl.
| | | |
|---|---|---|
| *A61Q 15/00* | (2006.01) | |
| *A61K 8/26* | (2006.01) | |
| *A61K 8/28* | (2006.01) | |
| *A61K 8/891* | (2006.01) | |

(52) U.S. Cl.
CPC .............. *A61Q 15/00* (2013.01); *A61K 8/26* (2013.01); *A61K 8/28* (2013.01); *A61K 8/891* (2013.01); *A61K 2800/87* (2013.01)

(58) Field of Classification Search
None
See application file for complete search history.

(56) References Cited

U.S. PATENT DOCUMENTS

| | | | | |
|---|---|---|---|---|
| 4,853,426 | A | * | 8/1989 | Chatterjee ...................... 524/100 |
| 5,100,930 | A | * | 3/1992 | Fukui et al. .................. 523/100 |
| 5,139,164 | A | * | 8/1992 | Stewart ......................... 220/788 |
| 2004/0241123 | A1 | * | 12/2004 | Popoff et al. .............. 424/70.12 |

FOREIGN PATENT DOCUMENTS

WO    WO 2006133725 A1 * 12/2006

OTHER PUBLICATIONS

Wessling, Carolina, et al., J Sci Food Agric 79:1635-1641 (1999).*
LookChem, date accessed Oct. 24, 2011, pp. 1-6.*
Down, "Antioxidants in polyolefins: By HPLC of the total solution extract", Oct. 18, 2010, pp. 1-2, [retrieved on Apr. 29, 2014]. Retrieved from the internet: <URL: www.separationsnow.com/details/ezine/sepspec24375ezine/Antioxidants-in-polyolefins-By-HPLC-of-the-total-solution-extract.html?tzcheck=1&tzcheck=1>.*
Al-Malaika, et al., The Antioxidant Role of A-Tocopherol in Polymers II. Melt Stablising Effect in Polypropylene, Polymer Degradation and Stability, vol. 64, Issue 1, Apr. 1999, pp. 145-156.
Irganox-3114, 1 page.
Irganox 1010, Phenolic Primary Antioxidant for Processing and Long-Term Thermal Stabilization (2 pages), Aug. 1998.

* cited by examiner

*Primary Examiner* — Ernst V Arnold
*Assistant Examiner* — Kyung Sook Chang
(74) *Attorney, Agent, or Firm* — Kathleen Y. Carter; Betty J. Zea; James C. Vago

(57) ABSTRACT

Antiperspirant products are described that include a dispensing package and an antiperspirant product contained within a chamber component of the dispensing package. The portion of the chamber component that comes into contact with the antiperspirant composition is made from a polymeric resin that is substantially devoid of phosphorus compounds.

8 Claims, No Drawings

ANTIPERSPIRANT PRODUCTS

FIELD OF THE INVENTION

The present invention is directed to antiperspirant products comprising a plastic dispensing package and an antiperspirant composition contained within the same.

BACKGROUND OF THE INVENTION

Non-pressurized antiperspirant compositions are typically packaged in plastic containers. And polyolefin resins are typically employed for molding the plastic containers. The resins can include processing aids, such as anti-oxidants, to improve the manufacturability and the stability of the molded container. However, it has been discovered that some processing aids can interact with antiperspirant actives and fragrances to produce an undesirable off-odor.

SUMMARY OF THE INVENTION

The present invention provides antiperspirant products that employ polyolefin dispensing packages capable of containing antiperspirant compositions including high efficacy actives and fragrances in the absence of the above-mentioned off-odor. In accordance with one exemplary embodiment, there has now been provided an antiperspirant product, comprising: (a) a dispensing package comprising a chamber for holding an antiperspirant composition, the chamber being made from a polyolefin resin that includes an anti-oxidant that is devoid of phosphorus compounds; and (b) an antiperspirant composition disposed within the chamber, the antiperspirant composition comprising a carrier material; an antiperspirant active having a metal to chloride ratio of less than or equal to 1.3; and a fragrance material.

DETAILED DESCRIPTION OF THE INVENTION

The present invention may be understood more readily by reference to the following detailed description of illustrative and preferred embodiments. It is to be understood that the scope of the claims is not limited to the specific components, methods, conditions, devices, or parameters described herein, and that the terminology used herein is not intended to be limiting of the claimed invention. Also, as used in the specification, including the appended claims, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent basis "about." it will be understood that the particular values form another embodiment. All ranges are inclusive and combinable.

The antiperspirant products of the present invention include a dispensing package that comprises a chamber for holding an antiperspirant composition. The chamber component of the package and any other component that comes into contact with the antiperspirant composition are made from a polymeric resin that is substantially devoid of fillers or processing aids that possess phosphorous compounds. Substantially devoid includes less than about 10%, 5%, 4%, 3%, 2%, and 1%, and 0%, by weight of the polymeric resin. Phosphite-containing anti-oxidants and process stabilizers are often included with polymeric resins to reduce polymer degradation during processing. Examples of these materials include ULTRANOX 626A Phosphite Antioxidant (commercially available from Crompton) and IRGAFOS 168 (commercially available from Ciba). Applicant has discovered however that phosphite-containing anti-oxidants can negatively interact with relatively high efficacy antiperspirant actives and some fragrance materials. An undesirable off odor is one manifestation of this negative interaction.

Polyolefin resins, such as, for example, polypropylene, are particularly suitable for manufacturing the package chamber. The polyolefin resins include an anti-oxidant to help reduce degradation during processing, but the anti-oxidant is substantially devoid of phosphorus compounds. Phenolic type anti-oxidants that are substantially free of phosphite, such as, for example, IRGANOX 1010 and IRGANOX 3114 (available from Ciba, are examples of a suitable anti-oxidant to use with the polyolefin resin. Injection molding is the preferred process for forming the package chamber out of the polyolefin resin. Other thermoforming processes can however be employed.

The antiperspirant compositions of the present invention include a carrier material, an antiperspirant active, and a fragrance material. Exemplary compositions can also include one or more optional ingredients, such as, for example, a structurant/thickener, emollients, moisturizes, and residue-masking agents.

Carrier materials can include, for example, a volatile silicone carrier whose concentration may be from about 20% or from about 30% but no more than about 80% or no more than about 60%, by weight of the composition. The volatile silicone may be cyclic, linear, and/or branched chain silicone. "Volatile silicone", as used herein, refers to those silicone materials that have measurable vapor pressure under ambient conditions. Non-limiting examples of suitable volatile silicones are described in Todd et al., "Volatile Silicone Fluids for Cosmetics", Cosmetics and Toiletries, 91:27-32 (1976). The volatile silicone may be a cyclic silicone having from at least about 3 silicone atoms or from at least about 5 silicone atoms but no more than about 7 silicone atoms or no more than about 6 silicone atoms. For example, volatile silicones may be used which conforms to the formula:

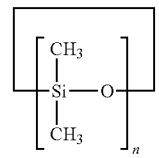

wherein n is from about 3 or from about 5 but no more than about 7 or no more than about 6. These volatile cyclic silicones generally have a viscosity of less than about 10 centistokes at 25° C. Suitable volatile silicones for use herein include, but are not limited to, Cyclomethicone D5 (commercially available from G. E. Silicones); Dow Corning 344, and Dow Corning 345 (commercially available from Dow Corning Corp.); and GE 7207, GE 7158 and Silicone Fluids SF-1202 and SF-1173 (available from General Electric Co.). SWS-03314, SWS-03400, F-222, F-223, F-250, F-251 (available from SWS Silicones Corp.); Volatile Silicones 7158, 7207, 7349 (available from Union Carbide); Masil SF-V (available from Mazer) and combinations thereof.

Suitable carrier materials can also include non-volatile organic fluids and non-volatile silicone fluids. Non-limiting examples of nonvolatile organic fluids include, but are not limited to, mineral oil, PPG-14 butyl ether, isopropyl myristate, petrolatum, butyl stearate, cetyl octanoate, butyl myristate, myristyl myristate, C12-15 alkylbenzoate, dipropylene glycol dibenzoate, PPG-15 stearyl ether benzoate and blends thereof, neopentyl glycol diheptanoate (e.g. Lexfeel 7 supplied by Inolex), octyldodecanol, isostearyl isostearate, octododecyl benzoate, isostearyl lactate, isostearyl palmitate, isononyl/isononoate, isoeicosane, octyldodecyl neopentanate, hydrogenated polyisobutane, and isobutyl stearate. Representative nonvolatile silicone fluids include those which conform to the formula:

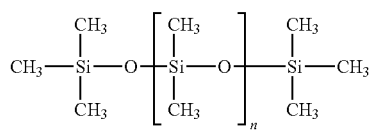

wherein n is greater than or equal to 1. These linear silicone materials may generally have viscosity values of from about 5 centistokes, from about 10 centistokes but no more than about 100,000 centistokes, no more than about 500 centistokes, no more than about 200 centistokes or no more than about 50 centistokes, as measured under ambient conditions. Specific non limiting examples of suitable nonvolatile silicone fluids include Dow Corning 200, hexamethyldisiloxane, Dow Corning 225, Dow Corning 1732, Dow Corning 5732, Dow Corning 5750 (available from Dow Corning Corp.); and SF-96, SF-1066 and SF18(350) Silicone Fluids (available from G.E. Silicones).

The antiperspirant compositions of the present invention include any particulate antiperspirant active suitable for application to human skin. The concentration of antiperspirant active in the composition should be sufficient to provide the finished antiperspirant product with the desired perspiration wetness and odor control. For example, the compositions of the present invention can contain particulate antiperspirant materials at concentrations ranging from about 0.1% to about 28% antiperspirant active by weight of the compositions, preferably from about 2% to about 22%, and more preferably from about 15% to about 20%. These weight percentages are calculated on an anhydrous unbuffered basis (exclusive of glycine, the salts of glycine, or other complexing agents). The particulate antiperspirant materials preferably have particle sizes of less than about 125 microns.

The antiperspirant active used herein has a metal to chloride molar ratio of less than or equal to about 1.3. Exemplary metal to chloride molar ratios include from about 1.3 to about 0.9, and from about 1.15 to about 1.3.

Particulate antiperspirant materials suitable for use herein are those that include any compound, composition or mixture thereof having antiperspirant activity. Astringent metallic salts are preferred antiperspirant materials for use herein, particularly the inorganic and organic salts of aluminum, zirconium and zinc, as well as mixtures thereof. Particularly preferred are the aluminum and zirconium salts, such as aluminum halides, aluminum hydroxy halides, zirconyl oxide halides, zirconyl hydroxy halides, and mixtures thereof.

Preferred aluminum salts are those represented by the formula:

$Al_2(OH)_aCl_b \cdot xH_2O$ wherein a is from about 0 to about 4.5; the sum of a and b is about 6; x is from about 1 to about 8; and wherein a, b, and x may have non-integer values. Particularly preferred are the aluminum chlorhydroxides referred to as "¾ basic chlorhydroxide," wherein a is about 4.5, "⅔ basic chlorhydroxide," wherein a is about 4, and aluminum chloride wherein a is about 0. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980. A general description of these aluminum salts can also be found in *Antiperspirants and Deodorants*, Cosmetic Science and Technology Series Vol. 20, 2nd edition, edited by Karl Laden. Mixtures of aluminum salts are described in British Patent Specification 1,347,950, Shin et al., published Feb. 24, 1974.

Zirconium salts are also preferred for use in the antiperspirant compositions. These salts are represented by the formula:

$ZrO(OH)_{2-a}Cl_a \cdot xH_2O$ wherein a is from about 0.5 to about 2; x is from about 1 to about 7; and wherein a and x may have non-integer values. These zirconium salts are described in Belgian Patent 825,146, Schmitz, issued Aug. 4, 1975. Particularly preferred zirconium salts are those complexes that additionally contain aluminum and glycine, commonly known as ZAG complexes. Such ZAG complexes contain aluminum chlorhydroxide and zirconyl hydroxy chloride of the formulae described above. Preferred ZAG salts are described in U.S. Pat. No. 4,331,609, Orr, issued May 25, 1982. Other such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978.

Polymer size distribution of the antiperspirant actives of the compositions of the present invention can be defined by the size exclusion chromatography method as described hereinafter using Gel Permeation Chromatography (GPC). Solid antiperspirant active salts are dissolved in 0.01M nitric acid and chromatographed using 5 µl injections in a series of three consecutive Waters µ Porasil Columns, 3.9×300 mm, 10 µm packing, A 0.01M nitric acid mobile phase is employed. Chromatograms are visualized using a Waters 410 Differential Refractometer. Samples are prepared immediately prior to analysis to prevent degradation. Relative peak areas and area ratios are calculated using a Waters Millennium Data System (Version 2.10 or equivalent). The peaks observed in the chromatogram are designated in order of appearance on the chromatogram as Peaks I-II (appear as a single peak) and Peaks III, IV and V. The area of Peaks III, IV and V corresponds to the relative concentration of aluminum polymer species exiting the column during the specified time period from the injected sample. For aluminum-zirconium salts, the area of Peaks I-II corresponds to the relative concentration of co-eluting aluminum and zirconium polymer species appearing initially on the chromatogram.

Prior to any analysis, the columns should be conditioned individually by repeated 100 µl injections of a 10% zirconium-aluminum tetrachlorohydrate glycine solution (containing at least 10% zirconium on a solid basis). Conditioning is complete when the area percent of Peaks I-II become relatively constant. During the conditioning process, the area percent of Peaks I-II will increase, and there will be reduction in retention for all peaks. Columns should be discarded when Peaks I and II are no longer resolved from Peak III.

Antiperspirant actives of the compositions of the present invention can have an average Peak IV area as defined by the methodology herein of at least about 7%, preferably at least about 20%, and more preferably at least about 25%.

Exemplary antiperspirant actives for use in the compositions of the present invention include aluminum chloride, aluminum dichlorohydrate, aluminum sesquichlorohydrate, aluminum zirconium tetrachlorohydrate, aluminum zirconium octachlorohydrate, aluminum zirconium tetrachlorohydrate glycine, aluminum zirconium octachlorohydrate glycine, and mixtures thereof.

A representative, non-limiting, list of fragrance materials that may be employed in antiperspirant compositions of the present invention includes anethole, benzaldehyde, decyl aldehyde, benzyl acetate, benzyl alcohol, benzyl formate, benzyl propionate, iso-bornyl acetate, camphene, cis-citral (neral), citronellal, citronellol, citronellyl acetate, paracymene, decanal, dihydrolinalool, dihydromyrcenol, methyl benzyl carbinyl acetate, dimethyl benzyl carbinyl acetate, dimethyl phenyl carbinol, eucalyptol, helional, geranial, geraniol, geranyl acetate, geranyl nitrile, cis-3-hexenyl acetate, dihydrocitronellal, d-limonene, linalool, linalool oxide, tetra-hydro linalool, alpha-methyl ionone, methyl nonyl acetaldehyde, methyl phenyl carbinyl acetate, laevo-menthyl acetate, menthone, iso-menthone, myrcene, myrcenyl acetate, myrcenol, nerol, neryl acetate, nonyl acetate, phenyl ethyl alcohol, phenyl acetaldehyde, alpha-pinene, beta-pinene, gamma-terpinene, terpineol, alpha-terpineol, beta-terpineol, terpinyl acetate, vertenex (para-tertiary-butyl cyclohexyl acetate), gamma-methyl ionone, undecalactone, undecylenic aldehyde, alpha-damascone, beta-damascone, amyl acetate, lemon oil, orange oil, and mixtures thereof.

The fragrance material may include the materials delineated above, or may include other perfumes/aromatic materials known to a person of ordinary skill in the art of creating fragrances. Typical fragrances are described in Arctander, Perfume and Flavour Chemicals (Aroma Chemicals), Vol. I and II (1969) and Arctander, Perfume and Flavour Materials of Natural Origin (1960). U.S. Pat. No. 4,322,308, issued to Hooper et al., Mar. 30, 1982 and U.S. Pat. No. 4,304,679, issued to Hooper et al., Dec. 8, 1981 disclose suitable fragrance materials including, but not limited to, volatile phenolic substances (such as iso-amyl salicylate, benzyl salicylate, and thyme oil red), essence oils (such as geranium oil, patchouli oil, and petitgrain oil), citrus oils, extracts and resins (such as benzoin siam resinoid and opoponax resinoid), "synthetic" oils (such as Bergamot™ 37 and Bergamot™ 430, Geranium™ 76 and Pomeransol™ 314); aldehydes and ketones (such as B-methyl naphthyl ketone, p-t-butyl-A-methyl hydrocinnamic aldehyde and p-t-amyl cyclohexanone), polycyclic compounds (such as coumarin and beta-naphthyl methyl ether), esters (such as diethyl phthalate, phenylethyl phenylacetate, non-anolide 1:4).

The values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An antiperspirant product, comprising:
   (a) a dispensing package comprising a chamber for holding an antiperspirant composition, the chamber being made from a polyolefin resin that includes an antioxidant which includes 0% of phosphorus compounds; and
   (b) an antiperspirant composition disposed within the chamber, the antiperspirant composition comprising:
      i) a carrier material;
      ii) an antiperspirant active comprising a zirconium-aluminum-glycine complex; and
      iii) a fragrance material.

2. The antiperspirant product of claim 1, wherein the polyolefin resin comprises polypropylene.

3. An antiperspirant product, comprising:
   (a) a dispensing package comprising a chamber for holding an antiperspirant composition, the chamber being made from a polyolefin resin that includes an antioxidant that is substantially devoid of phosphorus compounds; and
   (b) an antiperspirant composition disposed within the chamber, the antiperspirant composition comprising:
      i) a carrier material;
      ii) an antiperspirant active comprising a zirconium-aluminum-glycine complex; and
      iii) a fragrance material.

4. The antiperspirant product of claim 3, wherein the polyolefin resin comprises polypropylene.

5. The antiperspirant product of claim 3, wherein the carrier material comprises non-volatile organic fluids.

6. The antiperspirant product of claim 3, wherein the carrier material comprises from about 30% to about 80% by weight of a volatile silicone.

7. The antiperspirant product of claim 1, wherein the carrier material comprises non-volatile organic fluids.

8. The antiperspirant product of claim 7, wherein the carrier material comprises from about 30% to about 80% by weight of a volatile silicone.

* * * * *